United States Patent [19]

Matsen, III

[11] Patent Number: 5,779,710

[45] Date of Patent: Jul. 14, 1998

[54] JOINT REPLACEMENT METHOD AND APPARATUS

[76] Inventor: Frederick A. Matsen, III, 1853 E. Hamlin, Seattle, Wash. 98112

[21] Appl. No.: 668,578

[22] Filed: Jun. 21, 1996

[51] Int. Cl.⁶ .................................................. A61B 17/56
[52] U.S. Cl. ......................................................... 606/102
[58] Field of Search ............................. 606/102, 88, 89, 606/87, 96, 86

[56] References Cited

U.S. PATENT DOCUMENTS

| | | |
|---|---|---|
| 3,334,624 | 8/1967 | Schnieder et al. . |
| 4,487,203 | 12/1984 | Androphy . |
| 4,528,980 | 7/1985 | Kenna ............................ 606/102 |
| 4,549,319 | 10/1985 | Meyer . |
| 4,624,673 | 11/1986 | Meyer . |
| 4,667,664 | 5/1987 | Taylor et al. . |
| 4,703,751 | 11/1987 | Pohl . |
| 4,736,737 | 4/1988 | Fargie et al. . |
| 4,913,137 | 4/1990 | Azer et al. . |
| 4,952,213 | 8/1990 | Bowman et al. . |
| 5,108,396 | 4/1992 | Lackey et al. . |
| 5,342,366 | 8/1994 | Whiteside et al. ............... 606/86 |
| 5,562,675 | 10/1996 | McNulty et al. ................. 606/96 |
| 5,601,567 | 2/1997 | Swaiger et al. ................. 606/102 |
| 5,607,431 | 3/1997 | Dudasik et al. ................. 606/80 |

FOREIGN PATENT DOCUMENTS 1237553  6/1988  Canada .

OTHER PUBLICATIONS

"Humeral Head Prosthetic Arthroplasty: Surgical Relevant Geometric Considerations," Ballmer, et al., J. Shoulder Elbow Surg., vol. 2, pp. 296–304, 1983.

"Anatomic Determination of Humeral Head Retroversion: The Relationship of the Central Axis of the Humeral Head to the Bicipital Groove," Tillett, et al., J. Shoulder Elbow Surg., vol. 2, pp. 255–256, 1993.

"Total Shoulder Arthroplasty: Some Considerations Related to GlenoidSurface Contact," Ballmer, et al., J. Shoulder Elbow Surg., vol. 3, pp. 299–306, 1994.

"Total Shoulder Arthroplasty: Factors Influencing Prosthetic Sizing,"Iannotti, et al., Operative Techniques in Orthopaedics, vol. 4, No. 4, pp. 198–202, Oct. 1994.

"A New Humeral Prosthesis for the Japanese," Ishibashi, et al., pp. 273–276.

"The Normal Glenohumeral Relationships, An Anatomical Study of One Hundred and Forty Shoulders," Iannotti, et al., The Journal of Bone and Joint Surgery, vol. 74–A, No. 4, pp. 491–500, Apr., 1992.

"Articular Geometry of the Glenohumeral Joint," Soslowsky, et al., Clinical Orthopaedics and Related Research, Number 285, pp. 181–190, Dec. 1992.

"Quantitation of In Situ Contact Areas at the Glenohumeral Joint: A Biomechanical Study," Soslowsky, et al., Journal of Orthopaedic Research, vol. 10, pp. 524–534, 1992.

Primary Examiner—Guy V. Tucker
Attorney, Agent, or Firm—Barnes & Thornburg

[57] ABSTRACT

A method and apparatus are provided for replacing the articular surface of the ball of a ball and socket joint. The method comprises the steps of establishing the location of the intramedullary canal adjacent the ball of the joint, and placing a locating component, such as a reamer or broach, in the canal. The method further comprises sizing the articular surface of the ball to be replaced, placing on the component a resecting guide having an opening therein for receiving the component and a complementary surface to the articular surface of the ball to be replaced, rotating the component in a manner determined by the opening in the resecting guide, and resecting the ball in a manner determined by the orientation of the resecting guide.

1 Claim, 10 Drawing Sheets

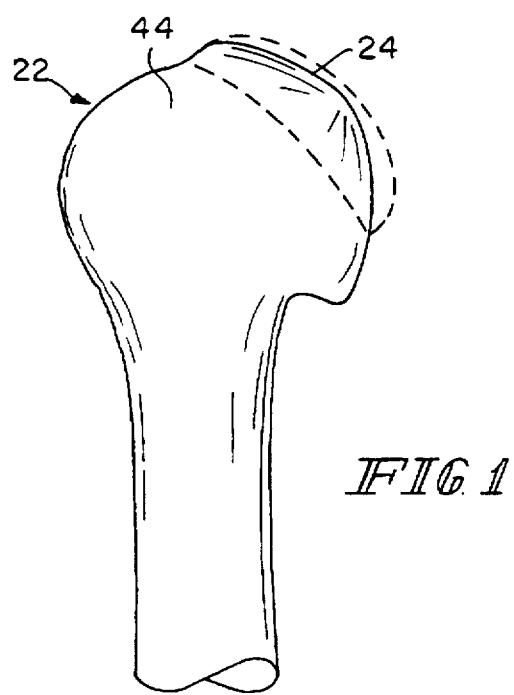
FIG. 1
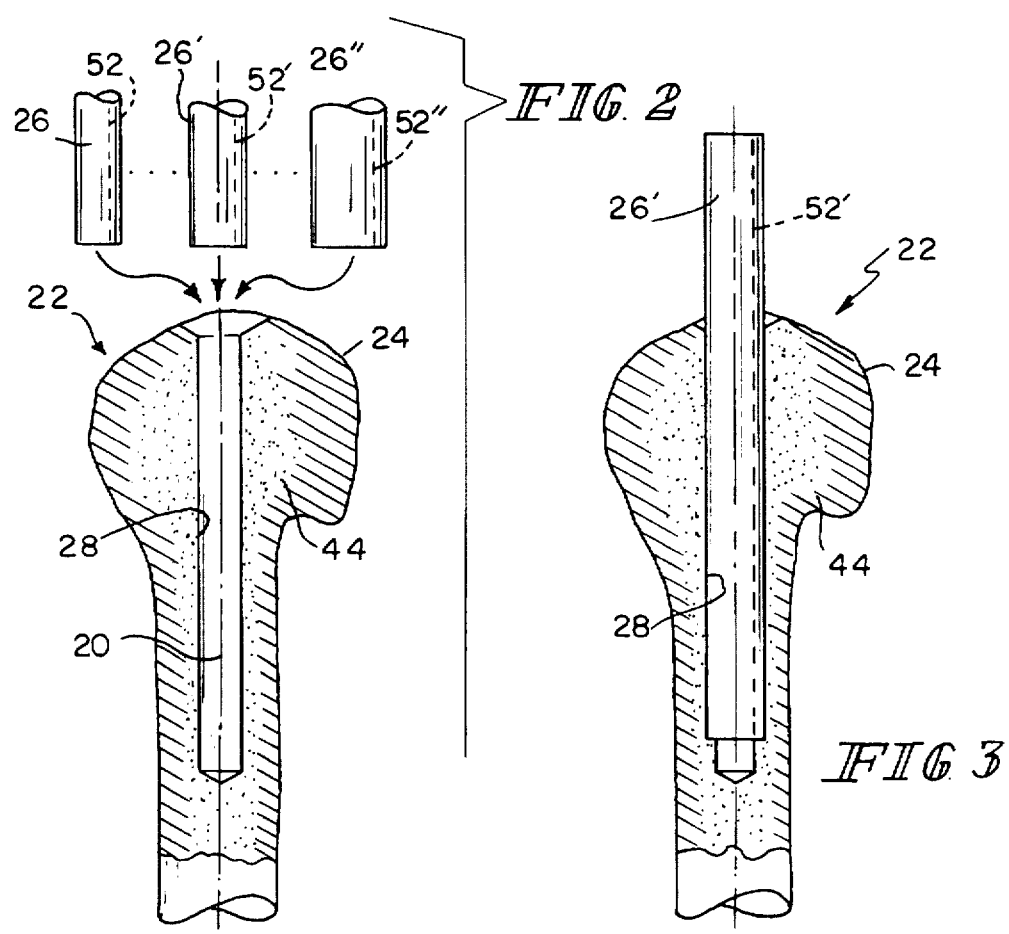
FIG. 2
FIG. 3

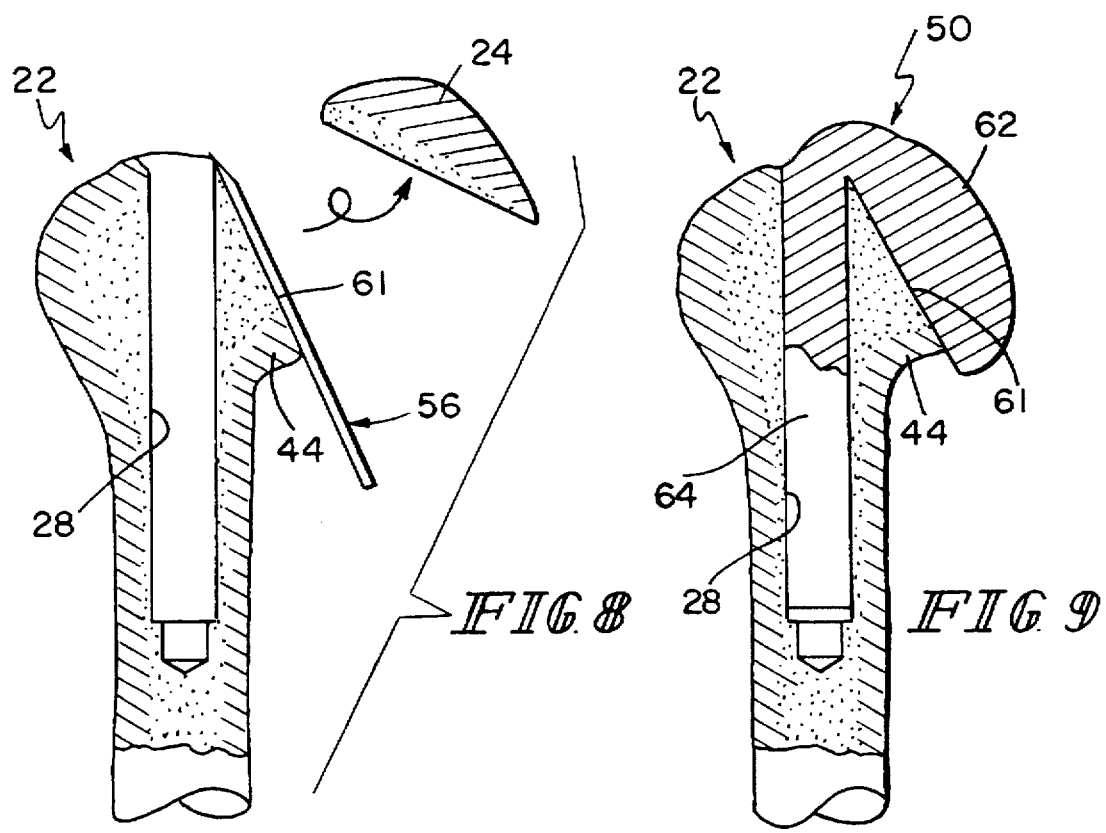

;# JOINT REPLACEMENT METHOD AND APPARATUS

BACKGROUND OF THE INVENTION AND DESCRIPTION OF THE PRIOR ART

Various techniques and apparatus for partial and complete anatomic joint replacement are known in the art. There are for example the techniques and apparatus described in the following listed U.S. Pat. Nos. 3,334,624; 4,487,203; 4,549,319; 4,624,673; 4,667,664; 4,703,751; 4,736,737; 4,913,137; 4,952,213; 5,108,396; and Canadian Patent 1,237,553. There are also the studies reported at: "Humeral Head Prosthetic Arthroplasty: Surgically Relevant Geometric Considerations," Franz T. Ballmer, M.D., et al., J Shoulder Elbow Surg., Vol. 2, pages 296–304, 1993; "Anatomic Determination of Humeral Head Retroversion: The Relationship of the Central Axis of the Humeral Head to the Bicipital Groove," Edward Tillett, M.D., et al., J Shoulder Elbow Surg., Vol. 2, pages 255–6, 1993; "Total Shoulder Arthroplasty: Some Considerations Related to Glenoid Surface Contact," Franz T. Ballmer, M.D., et al., J Shoulder Elbow Surg., Vol. 3, pages 299–306, 1994; "Total Shoulder Arthroplasty: Factors Influencing Prosthetic Sizing," Joseph P. Iannotti, M.D., PhD., et al., Operative Techniques in Orthopaedics, Vol. 4, No. 4, pages 198–202, October, 1994; "A New Humeral Prosthesis for the Japanese," Toru Ishibashi, M.D., et al., pages 273–276; "The Normal Glenohumeral Relationships, An Anatomical Study of One Hundred and Forty Shoulders," Joseph P. Iannotti, M.D., et al., The Journal of Bone and Joint Surgery, Vol. 74-A, No. 4, pages 491–500, April 1992; "Articular Geometry of the Glenohumeral Joint,", Louis J. Soslowsky, Ph.D., et al., Clinical Orthopaedics and Related Research, Number 285, pages 181–190, December, 1992; and, "Quantitation of In Situ Contact Areas at the Glenohumeral Joint: A Biomechanical Study," L. J. Soslowsky, et al., Journal of Orthopaedic Research, Vol. 10, pages 524–534, 1992. No representation is intended hereby that a thorough search of all pertinent prior art has been conducted or that no more pertinent prior art than that listed here exists. Nor should any such representation be inferred.

There are eight essential variables relating to humeral arthroplasty. These include: the diameter of curvature of the prosthesis; the percentage of the sphere with this diameter that will be used as prosthetic articular surface; the superior/inferior position of the articular surface relative to the humerus; the anterior/posterior position of the articular surface relative to the humerus; the medial/lateral articular aspect of the articular surface with respect to the humerus; the antero/posterior angulation (flexion/extension) of the articular surface relative to the prosthesis; the medial/lateral angulation (varus/valgus) of the prosthesis relative to the humerus; and, the rotational alignment of the prosthetic head with respect to the humeral axis. The goal of prosthetic arthroplasty is to duplicate the normal orientation of the humeral articular surface as well as its diameter of curvature and percentage of the sphere.

At present, no prosthetic arthroplasty system either establishes the diameter of curvature or the percentages of sphere of the humeral head to be replaced or determines the relationship of the articular surface to the orthopaedic axis of the medullary canal. As a result, the surgeon must guess at these important dimensions and relationships. Furthermore, no prosthetic system has previously been proposed which assures that when the medullary canal is reamed and the humeral head cut is made, the prosthetic articular surface will wind up in a position that duplicates the normal anatomy of the articular surface. Thus the challenges of anatomic humeral arthroplasty are to: determine the diameter of curvature of the articular surface; determine the percentage of the sphere; combine prosthetic design and rigorously guided bone cuts to assure that the desired result is achieved; and, by rigorously controlling the bone, to assure the desired relationship between the reamed medullary canal and the proximal humeral bone cut that uniquely and exactly fits the prosthesis.

SUMMARY OF THE INVENTION

The anatomic orthopaedic axis instrumentation and prosthesis of the invention are designed to: detect the orthopaedic axis of the medullary canal; determine the diameter of curvature and the percentage of sphere of the humeral head; uniquely relate the orthopaedic axis of the medullary canal to the diameter of curvature and percentage of sphere; and, prepare the humeral bone so that, when the anatomic orthopaedic axis prosthesis is inserted, the optimal orientation of the anatomic surface as well as optimal fit to the humeral bone is routinely and simply achieved.

It is recognized that preoperative two dimensional templating is only minimally useful in guiding the selection of a prosthesis and in preparation of the bone for optimal prosthetic fit and orientation. The prosthesis according to the invention is designed to replace the maximum amount of articular surface of the humerus with a prosthetic surface. The goal is to accommodate at least 90 percent of humeral variance using a combination of one-piece and modular components. The instrumentation system according to the invention includes a family of curvature/depth (percentage of sphere) gauges to enable ascertainment of the diameter of curvature of the humeral head and the percentage of the sphere represented by the articular surface. Making these two determinations is the first step in the prosthetic arthroplasty.

The next step in the prosthetic arthroplasty is to make a hole in the superior aspect of the articular surface through which medullary reamers or broaching tools are then inserted. Progressively larger medullary reamers are inserted and removed or the broach is inserted further until a snug fit is obtained, thereby establishing the orthopaedic axis. The depth of insertion of the reamers or broach is rigorously controlled so that it matches the depth of the stem of the prosthesis.

The next step in the arthroplasty is to place the articular surface gauges on the biologic humeral surface with the medullary reamer or broach in position and to measure the relationship of the two. This will include the determination of the medial and potentially the posterior offset of the center of the head with respect to the orthopaedic axis. After this point in the procedure the stem diameter, stem length, diameter of curvature of the humeral surface, and the percentage of the sphere to be replaced along with the posterior and medial offsets have all now been established. These factors combine to establish the desired prosthesis geometry, and therefore the desired prosthesis.

The next step in the arthroplasty is to use the selected articular surface gauge as a guide to the resection of the humeral head. The resected surface will exactly fit the prosthesis which exactly matches the anatomy. Because the articular surface gauge is oriented to the orthopaedic axis and because it represents the desired prosthesis geometry, using it as a cutting guide protects the rotator cuff, assures correct version of the cut, and assures that when the prosthesis is inserted, it will fit the bone cuts previously made. The next step of the procedure is to use the reamers or broach inserted along the orthopaedic axis for additional preparation of the medullary canal of the proximal humerus to receive the neck of the humeral component and the fixation fins.

Apparatus constructed according to the present invention provides a design and a method involving gauges having internal configurations complementary to various different sizes of articular surfaces of proximal humeral heads for trial sizing of the articular surface to be replaced. This suite of gauges and their engagement with a shaft, such as the shank of a reamer or broaching tool, which takes optimal advantage of the anatomic landmarks provided by the proximal humerus combine to establish the size of the prosthetic articular surface which best approximates the natural articular surface being replaced. This combination also establishes the prosthetic articular surface height, relative to the humeral resection, which best approximates the natural articular surface, and serves as a guide for that resection. This combination also establishes the degrees of the prosthetic articular surface offsets which best reflect the relative location of the natural articular surface.

According to an aspect of the invention, a method is provided for preparing a proximal humerus for receiving a prosthesis. The prosthesis comprises a stem for placement in the intramedullary canal and a head for articulation against the glenoid. The method comprises the steps of passing a shaft adjacent the proximal articular surface into the intramedullary canal, using the shaft in place in the canal and a gauge to determine the orientation and size of the articular surface of the natural humeral head relative to the shaft, and resecting the natural head using a resection guide. The gauge is selected from among a group of gauges of different sizes. Each gauge has a first portion for engaging the shaft, a second portion for sizing the articular surface, and a resection guide.

According to another aspect of the invention, a method is provided for preparation of a proximal humerus for receiving a prosthesis. The prosthesis comprises a stem for placement in the intramedullary canal and a head for articulation against the glenoid. The method comprises the steps of passing a shaft into the intramedullary canal to identify an axis of the humerus, the shaft entering the canal through the proximal humerus adjacent the proximal humeral articular surface, placing a gauge for determining the size of the articular surface of the natural humeral head relative to the shaft, providing a resection guide on the gauge, and resecting the proximal humeral articular surface to be replaced, thereby using the shaft as a guide to resect the proximal humeral articular surface being replaced, and replacing the proximal humeral articular surface with a prosthesis having a size determined by the gauge.

According to this aspect of the invention, the step of placing the gauge includes determining the location of the natural proximal humeral articular surface relative to the shaft.

Further according to this aspect of the invention, placing the gauge relative to the shaft comprises placing the gauge in contact with the shaft to establish the relative positions of the shaft and the gauge.

According to another aspect of the invention, an instrumentation system is provided for preparation of a proximal humerus for receiving a proximal humeral articular surface prosthesis. The prosthesis comprises a stem for placement in the intramedullary canal and an articular surface for articulation against the glenoid. The system comprises a shaft for entering the intramedullary canal from the proximal humeral head end adjacent the articular surface. The shaft has a guide portion. The system further comprises a plurality of gauges for determining the size, and cooperating with the shaft for determining the location, of the natural articular surface relative to the shaft. Each gauge has a characteristic size. The one gauge is selected that best fits the natural articular surface. Each gauge has a first portion which cooperates with the shaft guide portion to position the gauge relative to the shaft, a second portion for engaging the articular surface, and a gauge guide portion for guiding resection of the natural proximal humeral head.

According to yet another aspect of the invention, a method for replacing the articular surface of the ball of a ball and socket joint comprises the steps of establishing the location of the intramedullary canal adjacent the ball of the joint, and placing a locating device in the canal. The locating device has a component including a non-circular cross section transverse to its longitudinal extent. The method further comprises sizing the articular surface of the ball to be replaced, placing on the component a resecting guide having a complementary non-circular opening therein and a complementary surface to the articular surface of the ball to be replaced, rotating the component in a manner determined by the non-circular cross section of the opening in, and the orientation of, the resecting guide, and resecting the ball in a manner determined by the orientation of the resecting guide.

According to yet another aspect of the invention, a method for replacing the articular surface of the ball of a ball and socket joint comprises the steps of establishing the location of the intramedullary canal adjacent the ball of the joint, and placing a locating device in the canal. The method further comprises sizing the articular surface of the ball to be replaced, placing on the component a resecting guide having a complementary opening therein and a complementary surface to the articular surface of the ball to be replaced, rotating the component in a manner determined by the opening in the resecting guide, and resecting the ball in a manner determined by the orientation of the resecting guide.

According to another aspect of the invention, a method of sizing the articular surface of a ball of a ball and socket joint in preparation for replacement of at least a portion of the articular surface comprises the steps of providing gauges having different size internal surfaces complementarily configured to the articular surface, trying the gauges on the articular surface to be replaced and selecting the gauge providing the best fit.

According to another aspect of the invention, a method for determining the size of a replacement articular surface to replace at least one of the articular surfaces of a ball and socket joint comprises providing gauges having different size surfaces complementarily configured to one of the articular surfaces of the ball and socket joint, trying the gauges on the articular surface to which their complementarily configured surfaces are complementarily configured and determining the size of the replacement articular surface based upon the size of the gauge which best fits said one of the articular surfaces.

According to another aspect of the invention, a shaft is provided for insertion into the proximal end of the intramedullary canal of the proximal humerus. The shaft has a non-circular cross section transverse to its longitudinal extent along at least a part of its longitudinal extent. A plurality of gauges are provided for determining the size of an articular surface of the proximal humeral head to be replaced. Each gauge has an engaging portion for engaging the articular surface and a portion for receiving the non-circular cross section shaft.

The invention may best be understood by referring to the following detailed descriptions of illustrative embodiments and accompanying drawings. In the drawings:

BRIEF DESCRIPTION OF THE DRAWINGS

FIG. 1 illustrates a fragmentary side elevational view of the proximal head of a humerus with the original configuration of the articular surface illustrated in broken lines;

FIG. 2 illustrates a fragmentary sectional view of the proximal humeral head illustrated in FIG. 1 during the conduct of a step of a process according to the invention;

FIG. 3 illustrates a fragmentary sectional view of the proximal humeral head illustrated in FIG. 2 after completion of the step being conducted in FIG. 2;

FIG. 8 illustrates a fragmentary sectional view of the proximal humeral head illustrated in FIG. 6 after completion of the step being conducted in FIG. 6;

FIG. 9 illustrates a fragmentary section view of the proximal humeral head illustrated in FIGS. 2-6 and 8 after conduct of a process according to the invention;

DETAILED DESCRIPTION OF ILLUSTRATIVE EMBODIMENTS

Figure 4:
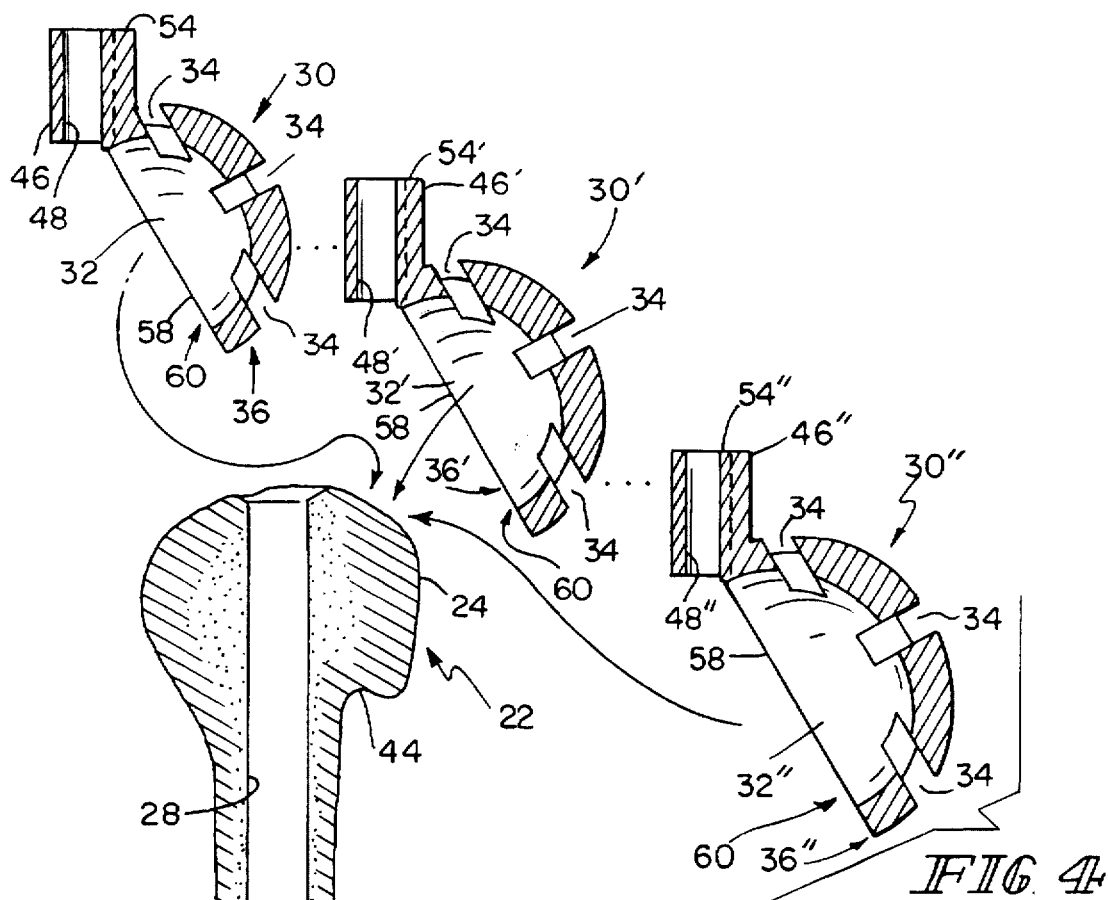
FIG. 4 illustrates a fragmentary sectional view of the proximal humeral head illustrated in FIGS. 2-3 during the conduct of a subsequent step of a process according to the invention.
Figure 5:
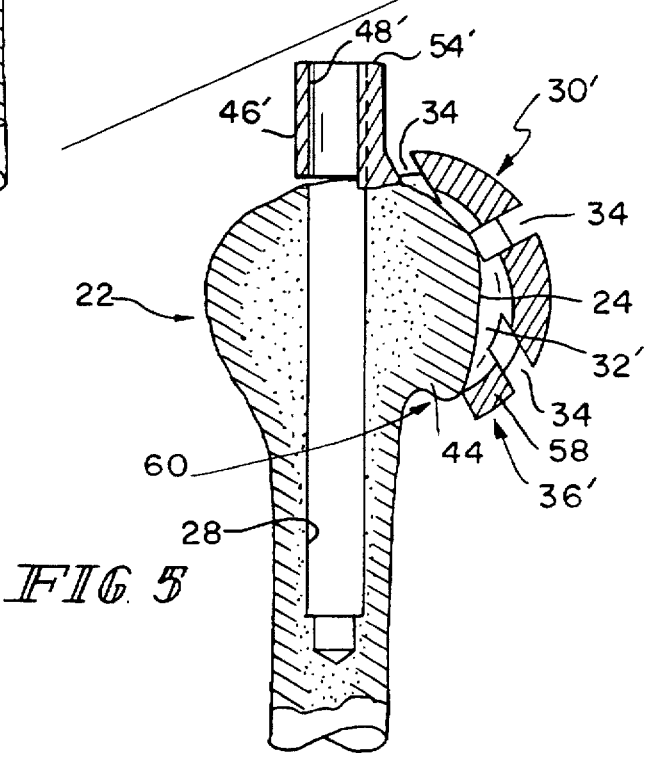
FIG. 5 illustrates a fragmentary sectional view of the proximal humeral head illustrated in FIG. 4 after completion of the step being conducted in FIG. 4.
Figure 6:
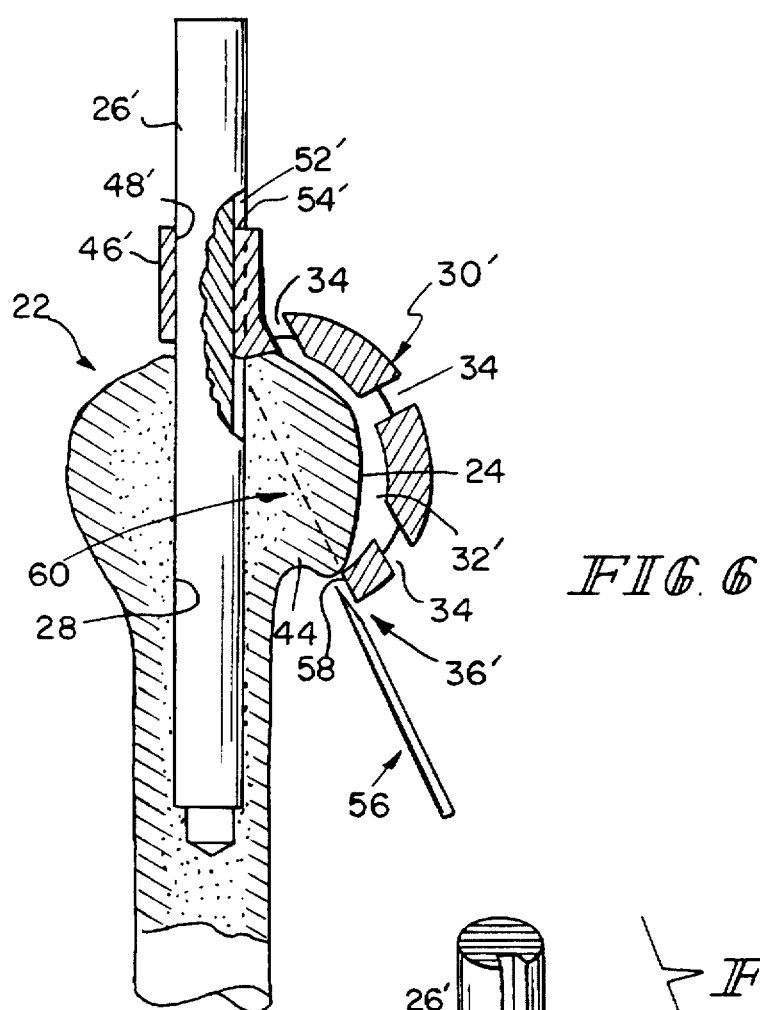
FIG. 6 illustrates a fragmentary sectional view of the proximal humeral head illustrated in FIGS. 2-5 during the conduct of a subsequent step in a process according to the invention.
Figure 7:
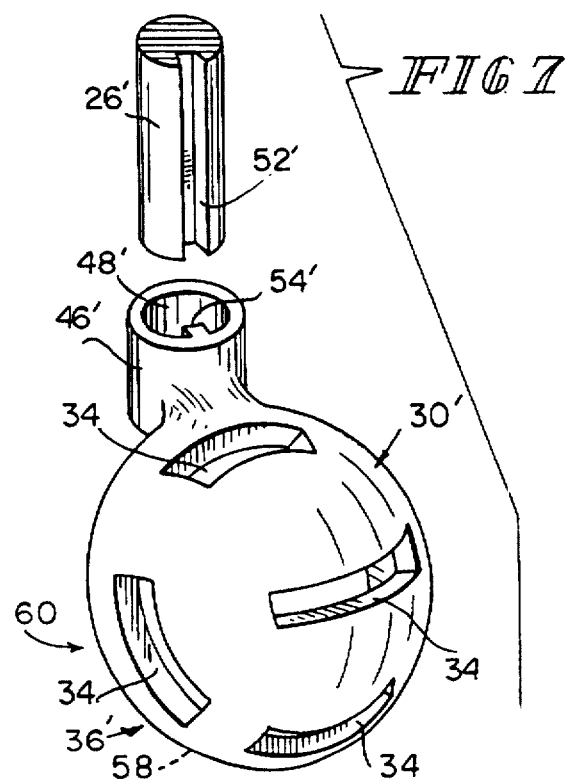
FIG. 7 illustrates an exploded fragmentary perspective view of certain details of an apparatus according to the present invention.
Figure 10:
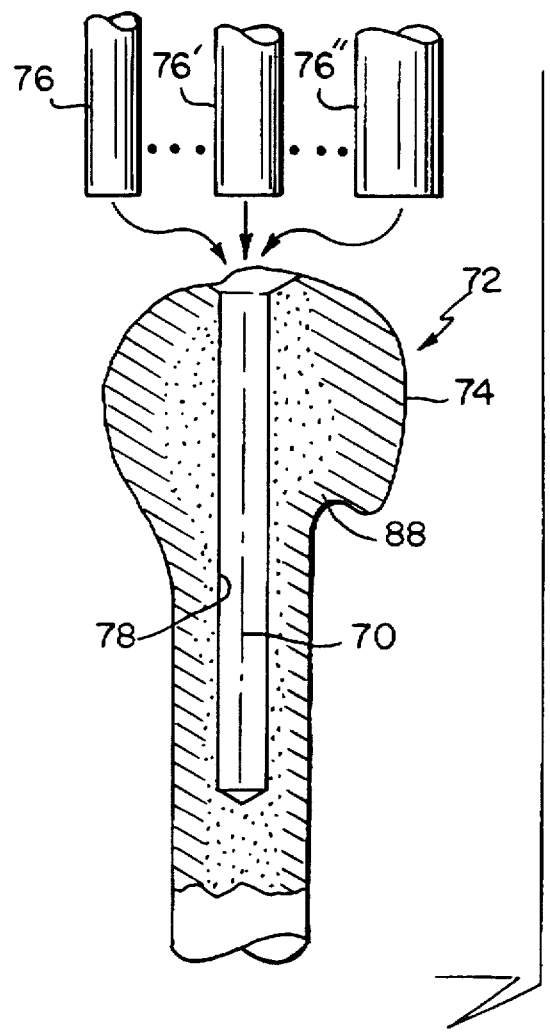
FIG. 10 illustrates a fragmentary sectional view of a proximal humeral head during the conduct of a step of a process according to the invention.
Figure 11:
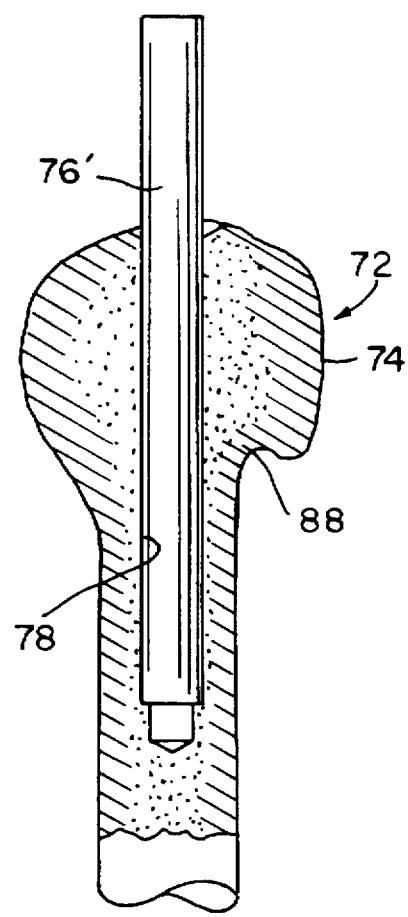
FIG. 11 illustrates a fragmentary sectional view of the proximal humeral head illustrated in FIG. 10 after completion of the step being conducted in FIG. 10.
Figure 12:
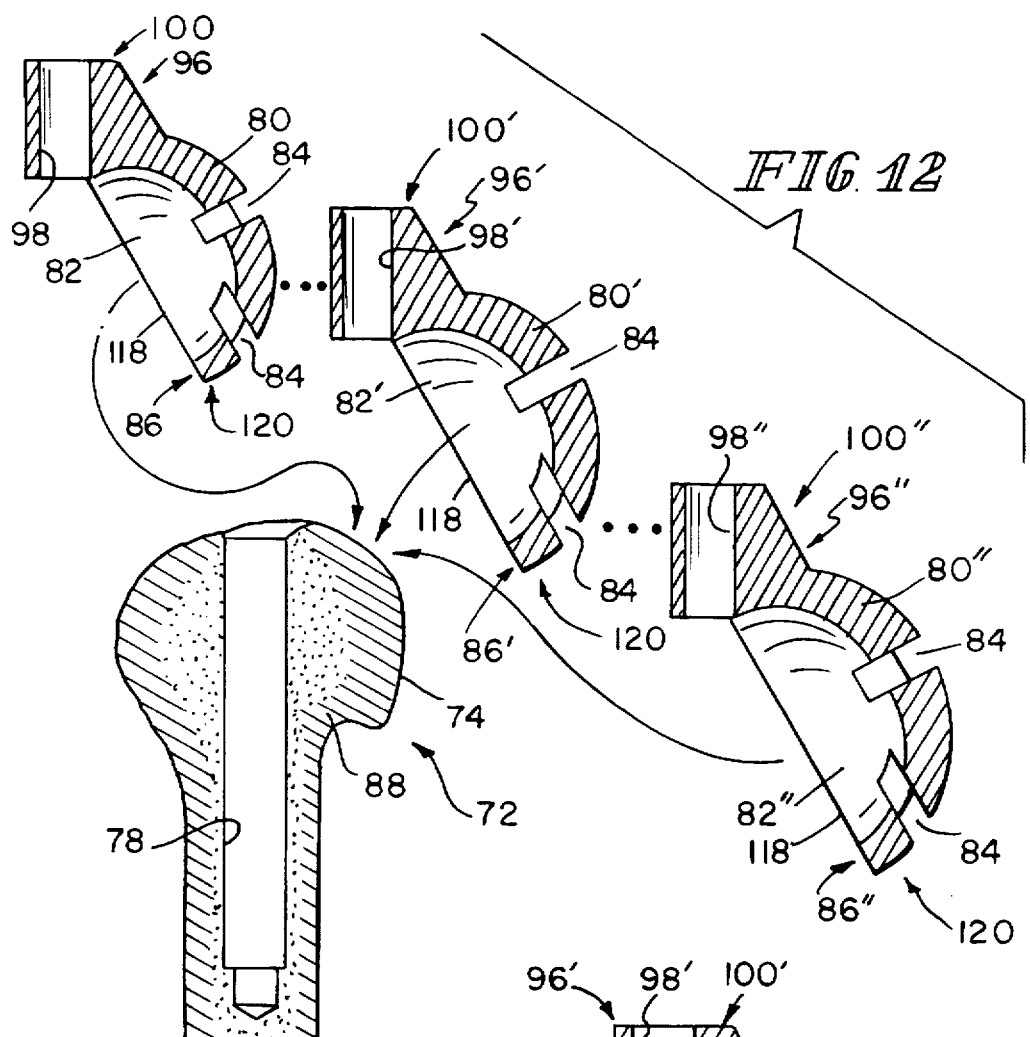
FIG. 12 illustrates a fragmentary sectional view of the proximal humeral head illustrated in FIGS. 10-11 during the conduct of a subsequent step of a process according to the invention.
Figure 13:
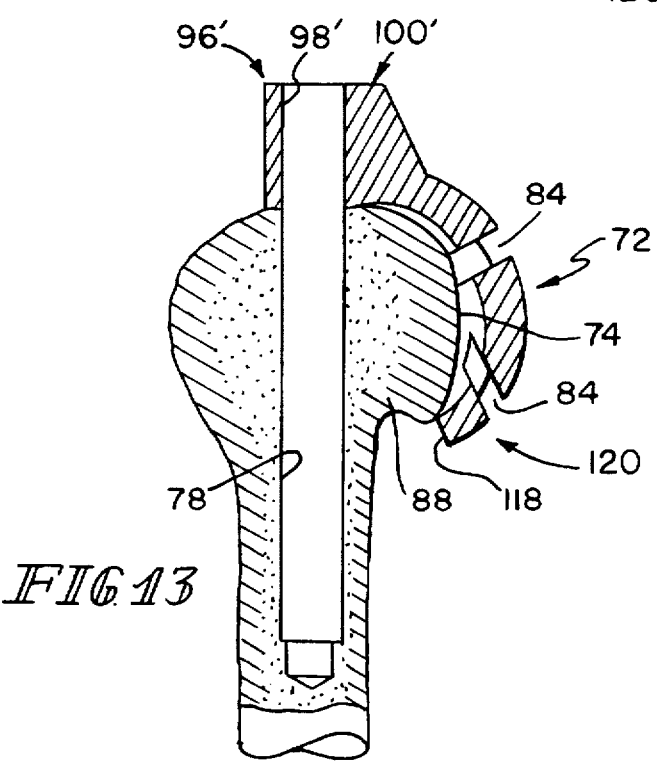
FIG. 13 illustrates a fragmentary sectional view of the proximal humeral head illustrated in FIG. 12 after completion of the step being conducted in FIG. 12.
Figure 14:
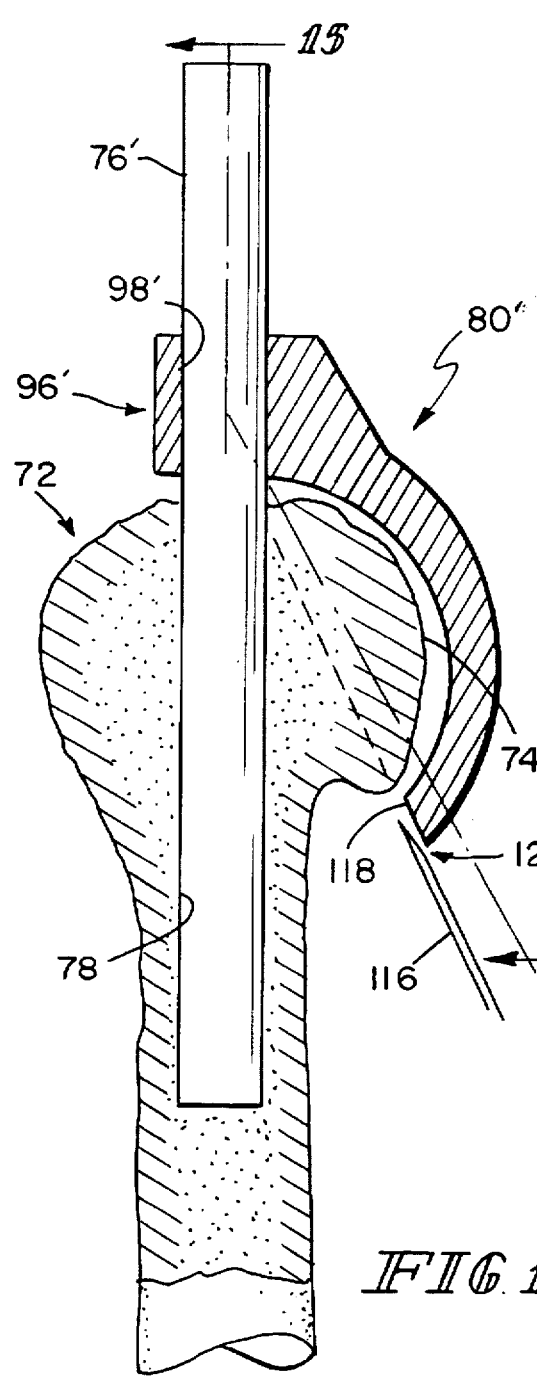
FIG. 14 illustrates a fragmentary sectional view of the proximal humeral head illustrated in FIGS. 10-14 during the conduct of a subsequent step in a process according to the invention.
Figure 15:
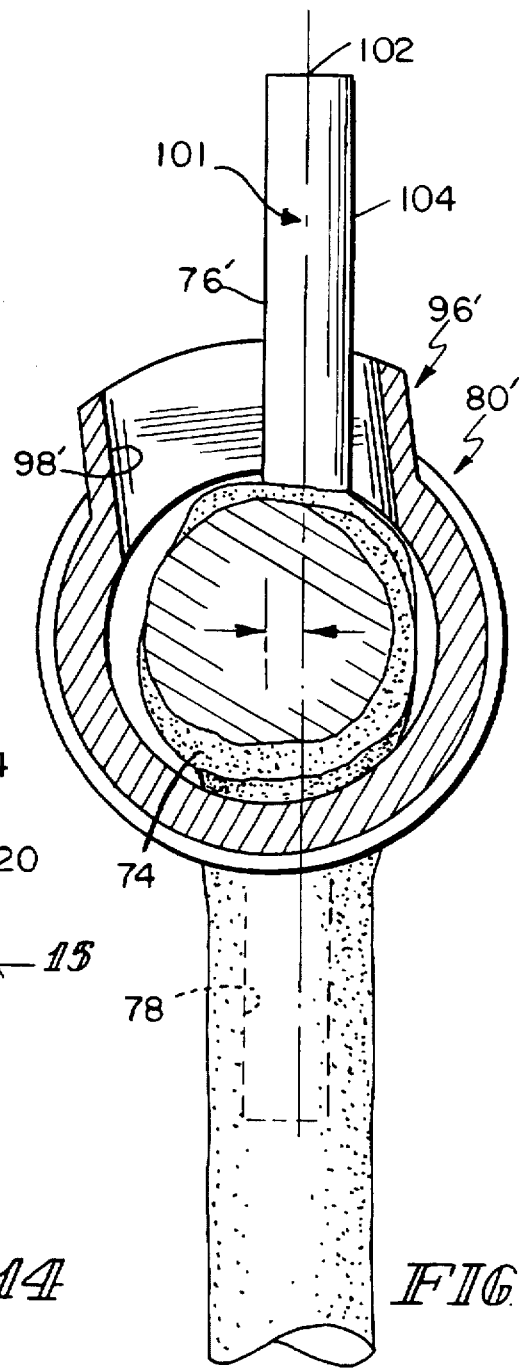
FIG. 15 illustrates a fragmentary, partial sectional view of the proximal humeral head illustrated in FIG. 14, taken generally along section lines 15—15 thereof.
Figure 16:
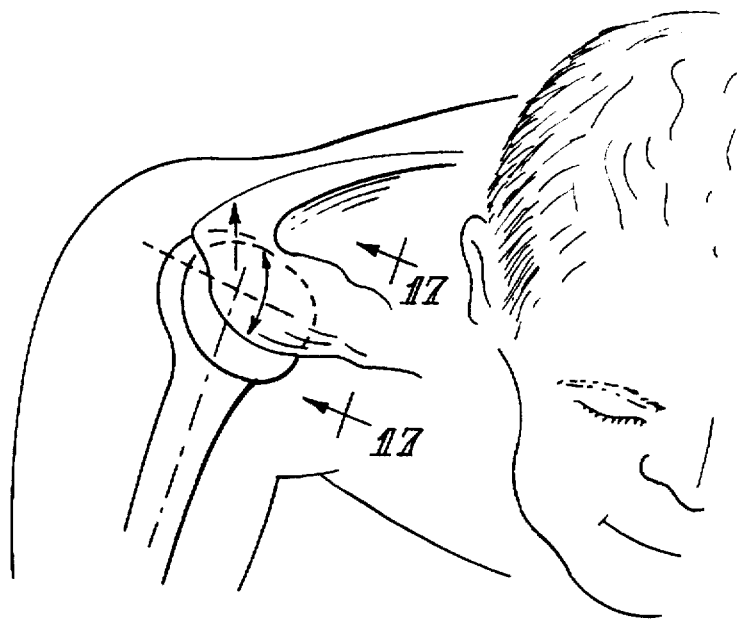
FIG. 16 illustrates a partly broken away fragmentary view of the proximal humeral head illustrated in FIGS. 10-15 illustrating certain parameters in the use of an apparatus according to the invention.

Referring now to FIGS. 1-9, in one embodiment of the method and apparatus which does not contemplate anterior or posterior offset of the prosthetic proximal humeral articular surface, the axis 20 of the proximal humeral head 22 is determined by reaming (FIG. 2) through the natural head adjacent the proximal humeral head's diseased natural articular surface 24 to be replaced using reamers 26, 26', 26" of increasing diameter until the largest diameter reamer 26' (FIG. 3) which will pass into the proximal humeral intramedullary canal 28 providing the snuggest fit is in place. The proximal humeral intramedullary canal 28 can also be opened, for example, by broaching, and so, as used throughout this application, "reaming" is intended to include broaching as well as other techniques that can be used to open the intramedullary canal 28 to its full extent.

Each gauge 30, . . . 30', . . . 30" (FIGS. 4-7) of a suite of such gauges comprises a generally part-spherical trial interior surface 32, . . . 32', . . . 32", respectively, complementary to a healthy natural articular surface. Each gauge 30, . . . 30', . . . 30" is provided with openings 34 through which the natural articular surface 24, and thereby the conformation of the gauge's interior surface 32, 32', . . . 32" to the natural articular surface 24, can be ascertained. The suite 30, . . . 30', . . . 30" of gauges includes gauges having not only different radii of curvature complementary to a healthy natural articular surface but also different, more or less straight sided or slightly flared skirt depths (short 36, . . . medium 36', . . . and long 36" in the illustrated example) to accommodate the height of the natural articular surface 24 from the surrounding proximal humeral bone tissue 44.

Each gauge 30, . . . 30', . . . 30" further comprises a cylindrical sleeve 46, . . . 46', . . . 46", respectively, providing a passageway 48, . . . 48', . . . 48", respectively, for slidably receiving a respective one of the various different diameter reamers 26, . . . 26', . . . 26". The term cylindrical as used herein to describe the internal surfaces of the sleeves 46, . . . 46', . . . 46" and external surfaces of the reamers 26, . . . 26', . . . 26" is used in its mathematical sense. That is, a cylindrical surface is a surface generated by a straight line moving in a closed path but remaining always parallel to another straight line.

The final diameter reamer, 26' in the illustrated example (FIG. 3), fits rather tightly into the proximal humeral intramedullary canal 28, and, as a result, once the final diameter reamer 26' is in place at the appropriate depth, defining an anatomic axis 20 of the proximal humerus 22, the reamer 26' serves not only as a location reference but also as an orientation (rotation) reference. That is, the final diameter reamer 26' resists rotation in the proximal humeral intramedullary canal 28. Consequently the final diameter reamer 26' is employed not only to establish an anatomic axis 20 of the natural articular surface 24 and thus of the prosthesis 50 which will follow, but also a rotational orientation of the natural articular surface 24 and thus of the prosthesis 50 about that axis 20. To this end, a reference is provided on each reamer 26, ... 26', ... 26". In the illustrated example, this reference comprises a keyway 52, ... 52', ... 52", perhaps best illustrated in FIG. 7, which extends along the reamer 26, ... 26', ... 26", respectively. The cylindrical sleeves 46, ... 46', ... 46" of the gauges 30, ... 30', ... 30", respectively, of the suite are complementarily configured at 54, ... 54', ... 54", respectively, to accommodate only one orientation of the gauges 30, ... 30', ... 30", respectively, of the suite on reamers 26, ... 26', ... 26".

If the interior size of a gauge 30, ... 30', ... 30" appears to be correct, but contact with the natural articular surface 24 appears through the visualization openings 34 to be less than optimal, the reamer 26, ... 26', ... 26" can be rotated slightly in the proximal humeral intramedullary canal 28 by the application of appropriate torque to reorient the gauge 30, ... 30', ... 30" more optimally to the anatomic landmarks the natural humerus 22 provides and thereby bring about a better fit. It should be understood that the appearance of the articular surface 24 under the gauge 30, ... 30', ... 30" will be affected by degenerative disease affecting surface 24. The proximal humeral articular surfaces illustrated in the various Figs. are relatively highly degenerated. Even so, the optimal fit even under these circumstances frequently can be fairly well ascertained by reference to the relationship between the superior aspect of the articular surface 24 and the surfaces 32, ... 32', ... 32".

Once the optimal fit has been established (FIG. 5) and the optimally fitting gauge 30' has been oriented on the natural articular surface 24, the surgeon may conduct a trial reduction of the joint to ascertain whether the optimal trial size gauge 30' provides proper capsular tension. This will not be a precise gauge of the fit because of the gauge's 30 ... 30', ... 30" wall thickness, but will provide a reasonable indication whether proper capsular tension will be achieved by the prosthesis 50 (FIG. 9) size indicated by the selected gauge 30'. If this trial indicates proper capsular tension, the joint is again dislocated and the natural articular surface 24 is resected 56 (FIG. 6) using the resection guide 58 provided at the base 60 of each gauge 30, ... 30', ... 30". At this time, any medial osteophytes which interfere with the replacement can also be removed.

Full use has now been made of the anatomic landmarks of the natural proximal humerus 22. The resected surface 61 bears the optimal relationship to these landmarks for subsequent fitting of the prosthetic 50 (FIG. 9) articular surface 62 of a size and orientation on its shank 64 determined by the resected surface 61 which, in turn, has been determined by the reaming 26' of the proximal humeral intramedullary canal 28, subsequent trial sizing of the gauges 30, ... 30', ... 30" on the reamer 26' shank, and orientation of the reamer 26' shank. The prosthetic articular surface 62 is a selected one of a suite of such surfaces. The selected prosthetic articular surface 62 is chosen, based upon the trialling, for its size and orientation on its shank 64. The gauge 30' and the reamer 26' are removed from the proximal humerus 22 along with the resected 56 natural articular surface 24. The shank 64 of the prosthetic 50 articular surface 62 is then fixed in the proximal humeral intramedullary canal 28 and the articular surface 62 on the resected surface 61 of the proximal humerus 22 using conventional techniques, such as, for example, adhesives, and the prosthetic joint is reduced and closed in a conventional manner.

Referring now to FIGS. 10–18, another embodiment of the method and apparatus is illustrated. This embodiment does contemplate anterior or posterior offset of the prosthetic proximal humeral articular surface. The axis 70 of the proximal humeral head 72 is determined by reaming (FIG. 10) through the natural head adjacent the proximal humeral head's diseased natural articular surface 74 to be replaced using reamers 76, ... 76', ... 76" of increasing diameter until the largest diameter reamer 76' (FIG. 11) which will pass into the proximal humeral intramedullary canal 78 providing the snuggest fit is in place.

Each gauge 80, ... 80', ... 80" (FIG. 12) of a suite of such gauges comprises a generally part-spherical trial interior surface 82, ... 82', ... 82", respectively, complementary to a healthy natural articular surface. Each gauge 80, ... 80', ... 80" is provided with openings 84 through which the natural articular surface 74, and thereby the conformation of the gauge's interior surface 82, ... 82', ... 82" to the natural articular surface 74, can be ascertained. The suite 80, ... 80', ... 80" of gauges includes gauges having not only different radii of curvature complementary to a healthy natural articular surface but also different, more or less straight sided or slightly flared skirt depths (short 86, ... medium 86' ... , and long 86" in the illustrated example) to accommodate the height of the natural articular surface 74 from the surrounding proximal humeral bone tissue 88.

Each gauge 80, ... 80', ... 80" further comprises a sleeve 96, ... 96', ... 96", respectively, providing a right somewhat oval-shaped cylindrical passageway 98, ... 98', ... 98", respectively, for receiving a respective one of the various different diameter reamers 76, ... 76', ... 76". Again, the term cylindrical as used herein to describe the passageways 98, ... 98', ... 98" and external surfaces of the reamers 76, ... 76', ... 76" is used in its mathematical sense.

Figure 17:
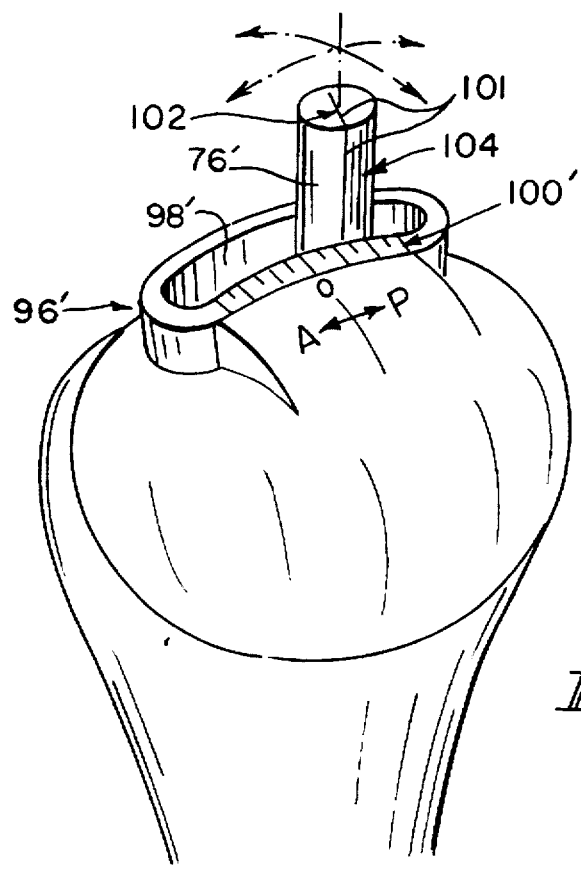
FIG. 17 illustrates a fragmentary perspective view of the proximal humeral head illustrated in FIGS. 10-16, taken generally along section lines 17—17 of FIG. 16.
Figure 18:
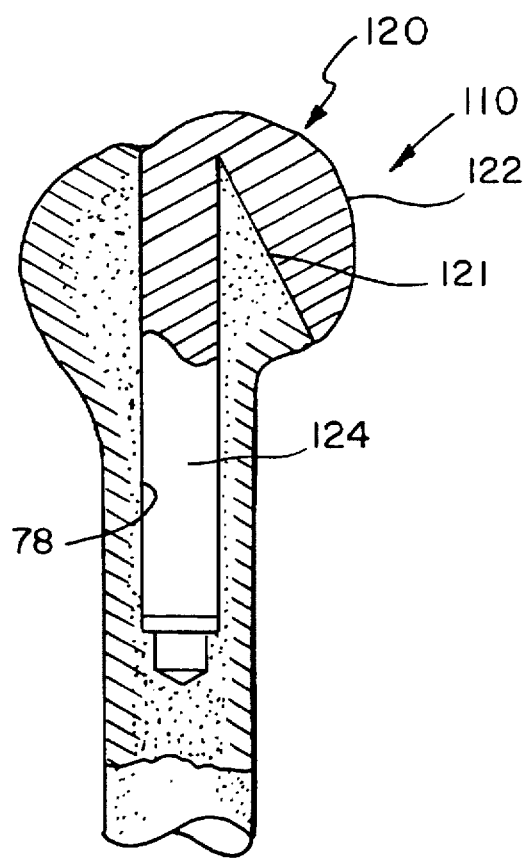
FIG. 18 illustrates a fragmentary section view of the proximal humeral head illustrated in FIGS. 10-17 after conduct of a process according to the invention.

Each gauge 80, ... 80', ... 80" is provided adjacent its sleeve 96, ... 96', ... 96" with a scale 100, ... 100', ... 100", best illustrated in FIG. 17, in millimeters, for example. An index 101 such as a scribed line or arrow is provided on the upper end 102 and/or along the side 104 of each reamer 76, ... 76', ... 76" adjacent its upper end 102. The indices 101 align with one of the indices of the scales 98, ... 98', ... 98" to establish the number of millimeters of offset of the anatomic axis 70 of the proximal humeral intramedullary canal 78 with respect to the articular surface 74 as represented by the scale 98' on the sleeve 96' of the optimally fitting gauge 80'. The prosthesis 110 (FIG. 18) is chosen based upon the trialling of the gauges 80, ... 80', ... 80" and the offsets, as determined by the relationship between the index 101 on the optimally fitting reamer 76' and the scale 98' on the optimally fitting gauge 80'.

Once these parameters have been established and the optimally fitting gauge 80' selected (FIG. 13), the optimally fitting gauge 80' can be oriented on the natural articular surface 74 and the joint can be trial reduced by the surgeon to ascertain capsular tension. Again, this trial reduction will not be precise because of the gauge's 80' wall thickness, but it will provide a reasonable indication of the adequacy of the capsular tension. If this trial indicates proper capsular tension, the joint is again dislocated and the natural articular surface 74 is resected 116 (FIG. 14) using the resection guide 118 provided at the base 120 of each gauge 80, ... 80', ... 80".

Full use has now been made of the anatomic landmarks of the natural proximal humerus 72. The resected surface 121 (FIG. 18) bears the optimal relationship to these landmarks for subsequent fitting of the prosthetic 120 articular surface 122 of a size and offset determined by the resected surface 121 which, in turn, has been determined by the reaming 76' of the proximal humeral intramedullary canal 78, subsequent trial sizing of the gauges 80, ... 80', ... 80" on the reamer 76' shank, and orientation of the optimally fitting gauge 80' with respect to the reamer 76' shank. The prosthetic articular surface 122 is a selected one of a suite of such surfaces. The selected prosthetic articular surface 122 is chosen, based upon the trialling, for its size and offset with respect to its shank 124. The gauge 80' and the reamer 76' are removed from the proximal humerus 72 along with the resected 116 natural articular surface 74. The shank 124 of the prosthetic 120 articular surface 122 is then fixed in the proximal humeral intramedullary canal 78 and the articular surface 122 on the resected surface 121 of the proximal humerus 72 using conventional techniques. The prosthetic joint is reduced and closed in a conventional manner.

Figure 20:
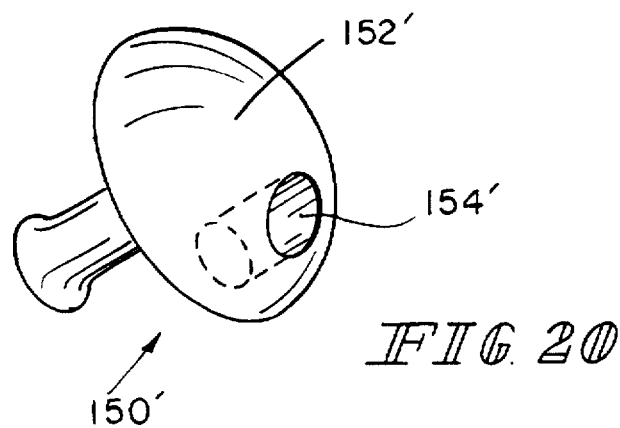
Figure 19:
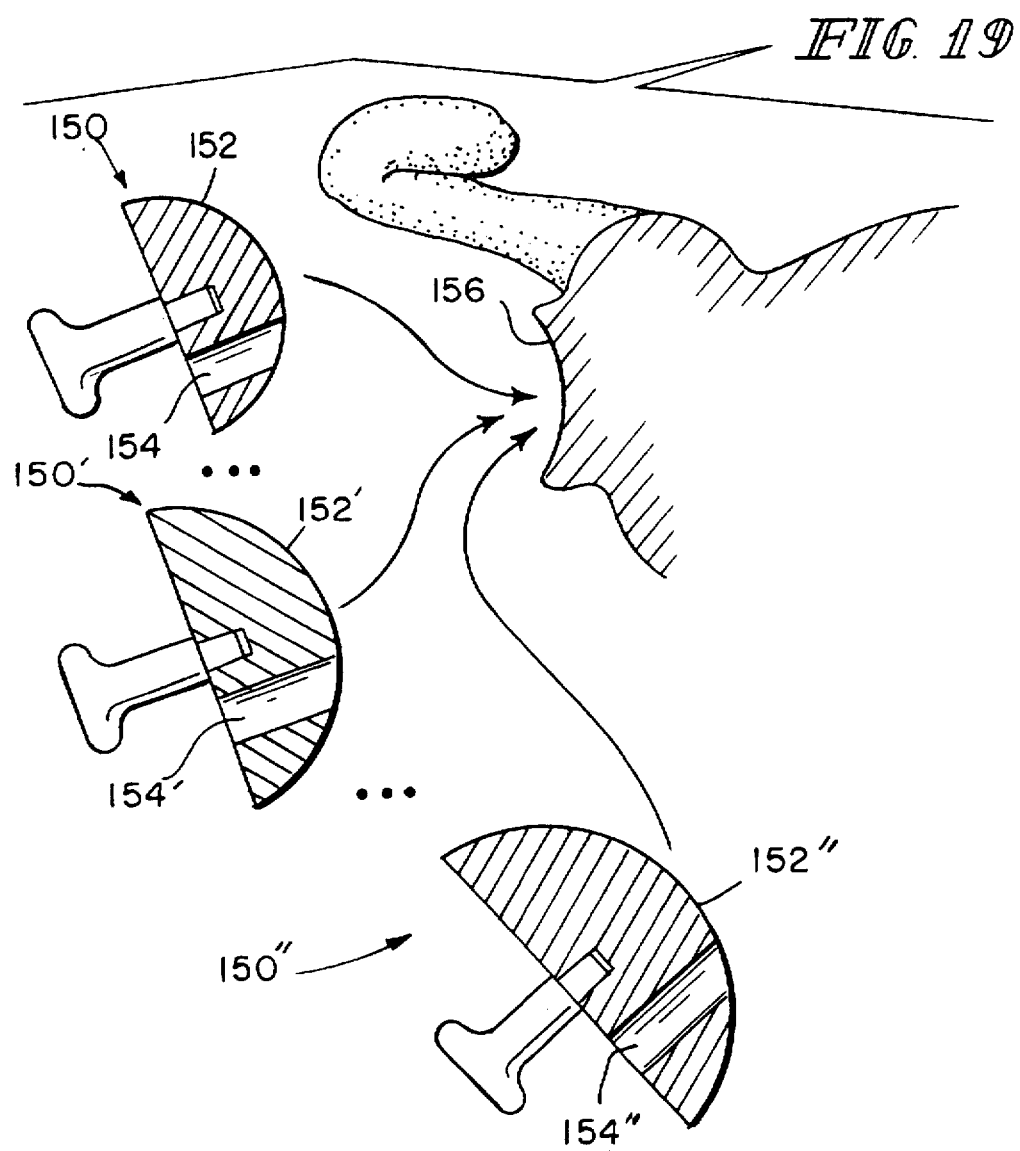
FIG. 19 illustrates a fragmentary sectional view of a glenoid during the conduct of a step of a process according to the invention; and, FIG. 20 illustrates a perspective view of certain details of an apparatus according to the present invention.

There may be circumstances such as, for example, extreme trauma to the natural proximal humeral articular surface, in which the surgeon cannot, or does not wish to, size the articular surface of the prosthesis based upon, or based solely upon, the condition of the natural proximal humeral articular surface. The embodiment of the present invention illustrated in FIGS. 19–20 contemplates a suite of gauges 150, ... 150', ... 150" whose exterior surfaces 152, ... 152', ... 152", respectively, represent various sizes of prosthetic proximal humeral articular surfaces. The gauges 150, ... 150', ... 150" are provided with openings 154, ... 154', ... 154", respectively, through which the degrees of conformity of surfaces 152, ... 152', ... 152" to a glenoid 156 (FIG. 19) can be ascertained and the optimally fitting gauge, for example, gauge 150', of the suite of gauges 150, ... 150', ... 150" selected by the surgeon. Once the radius of curvature of the optimally fitting prosthesis has been established, the remaining steps of the proximal humeral replacement may proceed as previously described or, in cases of extreme trauma, for example, the surgeon may refer to whatever other anatomic landmarks are helpful to complete the replacement.

I claim:

1. A shaft for insertion into the proximal end of the intramedullary canal of the proximal humerus, the shaft having a non-circular cross section transverse to its longitudinal extent along at least a part of its longitudinal extent, and a plurality of gauges for determining the size of an articular surface of the proximal humeral head to be replaced, each gauge having an engaging portion for engaging the articular surface and a portion for receiving the non-circular cross section shaft.

* * * * *